(12) United States Patent
Ebert et al.

(10) Patent No.: US 10,561,545 B2
(45) Date of Patent: Feb. 18, 2020

(54) ABSORBENT STRUCTURE AND ABSORBENT ARTICLE CONTAINING SAID ABSORBENT STRUCTURE

(71) Applicants: PAUL HARTMANN AG, Heidenheim (DE); GLATFELTER FALKENHAGEN GMBH, Pritzwalk (DE)

(72) Inventors: Anselm Ebert, Heidenheim (DE); Joerg Eilers, Heidenheim (DE); Stefanie Lutter, Pritzwalk (DE); Henning Roettger, Pritzwalk (DE)

( * ) Notice: Subject to any disclaimer, the term of this patent is extended or adjusted under 35 U.S.C. 154(b) by 386 days.

(21) Appl. No.: 15/538,906

(22) PCT Filed: Dec. 21, 2015

(86) PCT No.: PCT/EP2015/080708
§ 371 (c)(1),
(2) Date: Jun. 22, 2017

(87) PCT Pub. No.: WO2016/107772
PCT Pub. Date: Jul. 7, 2016

(65) Prior Publication Data
US 2017/0348166 A1  Dec. 7, 2017

(30) Foreign Application Priority Data

Dec. 29, 2014 (EP) .................................. 14200368

(51) Int. Cl.
*A61F 13/534* (2006.01)
*A61F 13/84* (2006.01)
(Continued)

(52) U.S. Cl.
CPC ........ *A61F 13/534* (2013.01); *A61F 13/8405* (2013.01); *A61L 15/28* (2013.01);
(Continued)

(58) Field of Classification Search
CPC .............. A61F 13/15203; A61F 13/534; A61F 13/8405; A61F 2013/15284;
(Continued)

(56) References Cited

U.S. PATENT DOCUMENTS 3,794,034 A * 2/1974 Jones, Sr. ......... A61F 13/15211
604/360
5,562,740 A 10/1996 Cook et al.
(Continued)

FOREIGN PATENT DOCUMENTS

DE  10 2009 055 951 A1  6/2011
DE  10 2010 006228 A1  8/2011
(Continued)

OTHER PUBLICATIONS

International Preliminary Report on Patentability dated Jul. 13, 2017 issued in connection with International Application No. PCT/EP2015/080708 with English Language translation (6 pages total).
(Continued)

*Primary Examiner* — Catharine L Anderson
(74) *Attorney, Agent, or Firm* — Tatonetti IP

(57) ABSTRACT

The present invention relates to an absorbent structure and an absorbent article containing said absorbent structure. The absorbent structure, having a sequence of layers connected together, comprises a first outer absorbent layer made from airlaid material, a second outer absorbent layer made from airlaid material, and a fluid storage layer made from airlaid material arranged between the first and second outer absorbent layers, wherein the airlaid material of the first outer absorbent layer comprises first cellulose fibres, the airlaid material of the second outer absorbent layer comprises second cellulose fibres and the airlaid material of the fluid storage layer comprises third cellulose fibres and superabsorbent components, wherein the first and second cellu-
(Continued)

lose fibres have a lower pH value than the third cellulose fibres and the pH value of the first and second cellulose fibres is less than 5.0.

28 Claims, 3 Drawing Sheets

(51) Int. Cl.
    *A61L 15/28*     (2006.01)
    *A61L 15/46*     (2006.01)
    *A61F 13/15*     (2006.01)
    *A61F 13/53*     (2006.01)

(52) U.S. Cl.
    CPC ..... *A61L 15/46* (2013.01); *A61F 2013/15284* (2013.01); *A61F 2013/530007* (2013.01); *A61F 2013/53445* (2013.01); *A61F 2013/53454* (2013.01); *A61F 2013/8411* (2013.01)

(58) Field of Classification Search
    CPC .......... A61F 2013/530007; A61F 2013/53445; A61F 2013/53454; A61F 2013/8411; A61L 15/46
    See application file for complete search history.

(56) References Cited

U.S. PATENT DOCUMENTS

| | | | |
|---|---|---|---|
| 6,462,252 B1* | 10/2002 | Runeman | A61L 15/46 604/360 |
| 6,852,904 B2 | 2/2005 | Sun et al. | |
| 7,834,233 B2* | 11/2010 | Cohen | A61F 13/8405 604/359 |
| 2002/0069988 A1 | 6/2002 | Yahiaoui et al. | |
| 2003/0100873 A1* | 5/2003 | Hermansson | A61F 13/15203 604/374 |
| 2005/0075617 A1* | 4/2005 | Vartiainen | A61F 13/534 604/360 |
| 2007/0020452 A1* | 1/2007 | Hamed | D06M 13/005 428/359 |

FOREIGN PATENT DOCUMENTS

| | | |
|---|---|---|
| EP | 0 138 179 A2 | 4/1985 |
| EP | 0 202 127 B1 | 11/1986 |
| EP | 0 832 320 B1 | 4/1998 |
| EP | 0 991 436 B1 | 4/2000 |
| EP | 1 191 915 B1 | 4/2002 |
| EP | 2 086 596 B1 | 8/2009 |
| EP | 2 184 042 A2 | 5/2010 |
| RU | 2671059 C1 | 10/2018 |
| WO | 00/35502 A1 | 6/2000 |
| WO | 00/74620 A1 | 12/2000 |
| WO | 2008/058563 A1 | 5/2008 |
| WO | 2008/138386 A1 | 11/2008 |

OTHER PUBLICATIONS

International Search Report dated Apr. 1, 2016 issued in connection with International Application No. PCT/EP2015/080708 with English Language translation (9 pages total).

* cited by examiner

ABSORBENT STRUCTURE AND ABSORBENT ARTICLE CONTAINING SAID ABSORBENT STRUCTURE

FIELD

The present invention relates to an absorbent structure having a sequence of interconnected plies comprising a first outer absorbent ply of airlaid material, a second outer absorbent ply of airlaid material and disposed between the first and second outer absorbent plies a liquid storage ply of airlaid material.

BACKGROUND

Absorbent structures find application in absorbent articles particularly in the hygiene sector as for example in infant diapers, femcare products or incontinence products, and also in the wound covering and wound treatment sector, as for example in wound contact materials.

Absorbent structures comprising an assembly of successive plies of airlaid material are known.

Thus DE 10 2009 055 951 A1 shows an absorbent structure consisting of at least three plies—a liquid acquisition layer, a subsequent liquid storage layer comprising SAP, and a liquid distribution layer—where preferably all the layers consist of a airlaid material. Further examples of a ply sequence of airlaid materials of this kind are known from DE 10 2010 006 228 A1 and EP 1 191 915 B1.

A problem with which absorbent structures are oftentimes hampered, irrespective of their construction, is that the liquid collected therein, specifically body fluid with organic components, constitutes a nutrient medium for the growth of bacteria and other microorganisms. Frequent consequences include skin problems due to skin irritation, and also development of odors.

A known counter to this fundamental problem is the establishment of acidic pH levels in collections of fibers through addition of acidic, pH-controlling substances or of acidic fibers.

Thus EP 0 138 179 A2 shows the production of acidic fibers and the effect thereof in neutralizing a basic test serum.

EP 0 202 127 B1 discloses absorbent hygiene articles featuring an arrangement of separate plies of pH-controlling components and SAP.

EP 0 991 436 B1 shows absorbent articles whose absorbent element comprises pH-controlling substances in the form of a partially pH-neutralized SAP and fluff pulp with a pH of less than 7. When the article is wetted, the product pH levels out at between 3.5 and 4.9, with effects including a reduction in enzyme activities by microorganisms present.

Additionally known, from EP 2 086 596 B1, are absorbent articles of typical construction having an absorbent element, the absorbent element including acidic cellulose fibers having a pH below/equal to 5.5 and an organic zinc salt for suppressing or reducing production of ammonia. Similar content can be found in WO 2008/138386 A1, which shows absorbent articles having absorbent elements comprising acidic cellulose fibers or acidic SAP with a pH below/equal to 5.5 and an addition of benzoic acid, hydroxy benzoic acid or an ester.

SUMMARY

It is an object of the present invention to provide an absorbent structure or absorbent article comprising such an absorbent structure, having not only absorbent properties but also properties of reducing or inhibiting microorganism growth, and providing the user of the absorbent structure with assurance of a relatively high degree of use comfort. In the use of the absorbent structure, moreover, the structure ought to be able to be disposed flexibly, and hence ought also to be able to be introduced with simplicity and flexibility in terms of process engineering into an ongoing process of production of an absorbent article.

This object is achieved in accordance with the invention by means of an absorbent structure having a sequence of interconnected plies comprising a first outer absorbent ply of airlaid material, a second outer absorbent ply of airlaid material and disposed between the first and second outer absorbent plies a liquid storage ply of airlaid material, wherein the airlaid material of the first absorbent ply includes first cellulose fibers, the airlaid material of the second outer absorbent ply includes second cellulose fibers and the airlaid material of the liquid storage ply includes third cellulose fibers and superabsorbent components, wherein the first and second cellulose fibers have a lower pH than the third cellulose fibers and wherein the pH of the first and second cellulose fibers is below 5.0. The pH of the first and second cellulose fibers and also the pH of the third cellulose fibers are determined by the method set out in the description.

With this invention it has been recognized that an airlaid material, in comparison to other types of nonwoven web, such as meltblown web or spunbonded web, constitutes a fiber material which has cavities, and thus forms interstices, and that equipping said material with acidic cellulose fibers having a pH below 5.0 represents an optimum combination for the interception and storage of liquids in an environment which inhibits or reduces microorganism growth. Although an acidic pH is desired for the purpose of reducing or inhibiting microorganism growth, the unhindered release of acidic agents into such skin-proximate utility regions of hygiene and wound management products is not unreservedly desirable. In contrast to an acidic equipping of fiber accumulations through addition of unbound pH control agents, such as acids or salts of acids, these acidic cellulose fibers in the airlaid material are able to act directly as an acidic biopolymer. An airlaid material with acidic cellulose fibers is able, without substantial leaching of the acidic component, to provide a permanent sheath around the liquid acquired and/or stored in the airlaid material.

As a result of the airlaid material both of the first and of the second outer absorbent plies including first and second cellulose fibers, respectively, having a pH below 5.0, these absorbent structures of the invention can be employed flexibly. Both the first and the second outer absorbent plies can be used as the body-facing ply in the application of the absorbent structure or in the case of the disposition of the absorbent structure within an absorbent article. Independently of the orientation of the absorbent structure, therefore, there is always a ply directed at the user and furnished with acidic pH conditions. Additionally, the other of the two outer absorbent plies, which constitutes the ply remote from the body and, in the embodiment of an absorbent hygiene article, therefore constitutes the clothing-facing ply is able to provide a further acquisition, distribution or storage venue with microorganism-growth-inhibiting conditions in the possible event of liquid mistakenly having traveled outside of the absorbent structure in the direction of the clothing side. The swellability of SAP is determined by the ionic strength and the pH of the environment, and so a not excessively acidic pH of the third cellulose fibers in the airlaid material of the liquid storage ply makes a positive contribution to the storage capacity of the SAP and hence also to the absorption capacity of the absorbent structure.

Airlaid material is understood here as an accumulation of staple fibers which are laid down in dry form, and hence of fibers having a finite or defined, preferably chopped, length. Staple fibers here may be natural fibers, such as cotton, fluff pulp or hemp, for example, or synthetic staple fibers of defined or chopped length based on natural fibers, such as viscose, for example, or based on polymers, such as polyolefins, polyamides, polyesters or combinations of polymers. In the case of a meltblown material or a spunbond material, in contrast, the freshly extruded meltblown fibers or spunbond fibers with infinite length are laid down to an accumulation of fibers immediately after their production process, and usually still in a tacky state. The airlaid material of the first outer absorbent ply, the second outer absorbent ply and the liquid storage ply therefore contains no meltblown fibers or spunbond fibers. The airlaid material may certainly be admixed with other components, such as different staple fibers or superabsorbent components in fibrous or particulate form.

The provision of plies of airlaid material is known to the skilled person. It is done by laying down the natural fibers or the synthetic staple fibers produced in a separate, upstream operation, in an airlay process. Where different staple fibers are used in the airlaid material, they are preferably mixed beforehand in a stream of air and then laid down according to customary web-forming processes. The airlaid material as such may be subjected to other measures for further processing as customary in the art, such as carding or consolidating, such as calendering or thermofixing, for example.

In the absorbent structure of the invention, in the first and second outer absorbent plies, there are preferably in each case more first cellulose fibers and second cellulose fibers than third cellulose fibers, and in the liquid storage ply there are preferably in each case more third cellulose fibers than first and/or second cellulose fibers included. Further preferably, at least 70 wt % of the fiber material of the respective airlaid material of the first and/or second outer absorbent plies consist of first cellulose fibers and second cellulose fibers, respectively, and at least 70 wt % of the fiber material of the airlaid material of the liquid storage ply consist of third cellulose fibers.

Especially preferred is an absorbent structure wherein the airlaid material of the first and/or second outer absorbent plies includes no third cellulose fibers. Especially preferably there are no third cellulose fibers included in the airlaid material of both outer absorbent plies. Especially preferred is an absorbent structure wherein the airlaid material of the liquid storage ply includes no first or second cellulose fibers. The understanding that forms the basis for the statements made above is that none of the other third or second or first cellulose fibers are deliberately admixed to the airlaid material of the respective ply composed of first or second cellulose fibers or third cellulose fibers, respectively. However, this is not to rule out the possibility of individual fibers from the respective ply protruding into the neighboring ply in the boundary regions between the individual respective plies. Particularly in the case of an in-line production process, this may be occasioned by direct, layered deposition of airlaid material plies.

In one advantageous embodiment of the absorbent structure, the first and/or second cellulose fibers have a pH below 4.7, preferably below 4.5, preferably below 4.2, and further preferably a pH above 3.2, further preferably above 3.5, further preferably above 3.7, further preferably above 3.9.

In order to promote the aspect of the advantageous effects of acidic pH for the reduction or inhibition of the growth of microorganisms and/or else reduction or inhibition of odors given off, in particular, the third cellulose fibers in the liquid storage ply also have a pH below pH 7. Especially preferably the third cellulose fibers have a pH below 6.7, further preferably below 6.5, further preferably below 6.3, and further preferably above pH 5.0, further preferably above 5.5, further preferably above 5.7, further preferably above 5.9.

In one preferred embodiment, the absorbent structure is designed such that the pH of the first and/or second cellulose fibers differs from the pH of the third cellulose fibers by not less than 0.5, preferably not less than 0.7, further preferably not less than 0.9, further preferably not less than 1.0, further preferably not more than 3.0, further preferably not more than 2.5, further preferably not more than 2.0.

Preferably, the absorbent structure includes the first and second cellulose fibers of the first and second outer absorbent plies in a total proportion of 20-50 wt %, preferably 25-45 wt %, further preferably 30-40 wt % based on the combined weight of the sequence of interconnected plies.

As first, second and third cellulose fibers it is possible to use fibers of any origin, provided cellulose is included, as in the case of natural fibers, e.g., bamboo fibers, cotton fibers or wool, and fluff pulp obtained therefrom, or where cellulose serves as starting material for the further processing or processing to regenerated fibers obtained therefrom, such as viscose fibers, for example. With more particular preference the first and/or second cellulose fibers and/or the third cellulose fibers comprise cellulosic fibrous material from the group of cotton fibers and/or fluff pulp. With further preference the first, second and/or third cellulose fibers consist of cellulosic fibrous material from the group of cotton fibers and/or fluff pulp. With more particular preference it is possible to use the identical fibers for the first and second cellulose fibers. Especially preferably, both for the first and second and for the third cellulose fibers, fluff pulp fibers are used which differ in accordance with the invention in their pH values. First and/or second cellulose fibers having a pH below pH 5.0 based on fluff pulp may be acquired from Weyerhaeuser, Wash., USA, for example.

The first and/or second cellulose fibers having a pH below pH 5.0 are preferably reaction products of cellulosic fibrous material, such as cotton fibers or fluff pulp in particular, with polycarboxylic acids or salts thereof and/or polyacrylic acids or salts thereof. Acidic cellulose fibers may be produced, for example, by the method shown in EP 0 832 320 B1 or in U.S. Pat. No. 6,852,904 B2. The polycarboxylic acids or salts thereof that are used for the reaction process may be taken in particular from the group of maleic acid, tartaric acid, citric acid, 1,2,3-propanetricarboxylic acid, 1,2,3,4-butanetetracarboxylic acid, and salts thereof.

The airlaid material of the first and/or second outer absorbent plies preferably includes no superabsorbent components. The avoidance of superabsorbent components in the outer plies is advantageous in order to prevent the risk of possible blocking directly at the outer layers. The superabsorbent components are introduced in the liquid storage ply preferably in order substantially to immobilize the liquid there by means of the superabsorbent components. The superabsorbent components of the liquid storage layer are preferably present in a proportion of not less than 25 wt %, preferably not less than 30 wt %, preferably not less than 35 wt %, further preferably not less than 40 wt %, further preferably not more than 70 wt %, further preferably not more than 60 wt %, further preferably not more than 50 wt % based on the combined weight of the sequence of interconnected plies. The superabsorbent components (8) are preferably in the form of SAP particles and/or SAP fibers, especially based on surface-crosslinked polyacrylates, which further preferably are partially neutralized.

In one advantageous development, the absorbent structure is equipped with binding agents. Thus, in particular, the airlaid material of the first and/or second outer absorbent plies includes binding agents, preferably binding fibers, further preferably binding fibers in the form of bi- and/or more-component fibers. In particular, the binding fibers may comprise thermoplastic materials, such as, in particular, polyesters and/or polyolefins. Bicomponent fibers with components having different melting points are used advantageously. With more particular advantage it is possible to use bicomponent fibers of polyethylene terephthalate and polyethylene. Thermoplastic fibers in the outer absorbent plies make an advantageous contribution to conducting the liquid into the liquid storage ply. Consequently, in particular, the airlaid material of the liquid storage ply includes no binding fibers, preferably no binding agents.

The airlaid material of the first outer and/or second outer absorbent plies preferably includes binding fibers in a total proportion of 2-10 wt %, preferably 2-7 wt %, further preferably 2-6 wt %, further preferably 3-6 wt %, further preferably 4-6 wt % based on the combined weight of the sequence of interconnected plies.

The sequence of interconnected plies includes first and second outer surfaces. In one preferred development of the absorbent structure, the first and/or second outer surfaces include a binding agent coating. The binding agent coating may more particularly be based on a dispersed polymer, especially an ethylene-vinyl acetate copolymer. A binding agent coating on the surface of the first and/or second outer absorbent plies may well assist advantageously, as a result of the fiber incorporation, with the capillary effect and transfer function of the outer plies, especially when binding fibers are present in the first and/or second outer plies. A binding agent coating also makes an advantageous contribution to abrasion resistance of the surfaces, and this, among other things, is positive in the case of direct use and also in the case of subsequent fabrication of an absorbent article in a mechanical production process.

In one preferred embodiment of the inventive concept of providing an absorbent structure which can be disposed with maximum flexibility in use or in the process of producing an absorbent hygiene article, the first and second absorbent plies have identical properties. The first and second outer absorbent plies are preferably identical with regard to one property at least, this property being taken from the group containing basis weight, pH of first or second cellulose fibers, chemical composition or natural provenance or origin of first and second cellulose fibers, weight fraction of first or second cellulose fibers, weight fraction of binding fibers, and fiber blend used for the airlaid material.

Especially preferably, the first and second outer absorbent plies are at least identical with regard to the pH of the first and second cellulose fibers.

Especially preferably, the first and second outer absorbent plies are identical at least with regard to the chemical composition or the natural provenance or the origin of the first cellulose fibers and second cellulose fibers.

With further preference, the first and second outer absorbent plies are identical with regard to the pH of the first and second cellulose fibers and with regard to the chemical composition or the natural provenance or the origin of the first and second cellulose fibers.

With further preference the first and second outer absorbent plies are identical with regard to the pH of the first and second cellulose fibers and to the weight fraction of first and second cellulose fibers.

Especially preferably, the first and second outer absorbent plies are identical with regard to the pH of the first and second cellulose fibers and in terms of the chemical composition or the natural provenance or the origin of the first and second cellulose fibers and with regard to the weight fraction of first and second cellulose fibers.

In one especially preferred embodiment, the first and second outer absorbent plies are identical with regard to all properties.

In a further-preferred development for obtaining an absorbent structure which can be disposed flexibly, the sequence of interconnected plies has mirror symmetry, meaning that in the case of an imaginary cross section through the sequence of interconnected plies, the plies may be imaged onto themselves by means of axial mirroring at their axis of symmetry. In the direction both of one and of the other surfaces of the sequence of interconnected plies, there are the same number of plies, and in particular these plies are a match in their functional furnishing, further in particular at least in one property taken from the group containing basis weight, pH of first or second cellulose fibers, weight fraction of first or second cellulose fibers, chemical composition or natural provenance or origin of the first and second cellulose fibers, weight fraction of binding fibers, and fiber blend used for the airlaid material.

The sequence of interconnected plies consists in particular of the first and second outer absorbent plies and disposed between them the liquid storage ply.

The sequence of interconnected plies may be obtained by the joining of the first and second absorbent plies and of the liquid storage ply, produced in separate process steps. Hence it is possible for the airlaid material plies, deposited for example on auxiliary carrier materials, such as tissue or nonwoven, for example, or fixed on corresponding auxiliary carrier materials, to be connected to one another with fixing agent, such as adhesive, ultrasound. The sequence of interconnected plies may alternatively also be obtained by means of in-line process through the successive deposition of the individual plies.

Consolidation of the sequence of interconnected plies may contribute to the capillary effect and hence also storage effect of the overall absorbent structure. The sequence of interconnected plies is consolidated in particular by pressure and/or by temperature, especially when binding fibers are present in the first and/or second outer absorbent plies and/or in the case of a binding agent coating on the outer surfaces. Consolidation takes place in particular without formation of embossed patterns, which may possibly—especially with absorbent structures of low thickness—represent the risk of breakage points in the absorbent structure. For this purpose, the consolidation is accomplished preferably using smooth rollers.

The absorbent structure has a thickness of preferably 1-6 mm, more preferably 2-5 mm, further preferably 2-4 mm. The thickness here is measured with a mechanical thickness tester having a measuring area of 25 $cm^2$, using a test pressure of 5 $g/cm^2$. The test specimens here have been adapted to the standard conditions of 23° C. at 50% relative humidity. Absorbent structures having thick-nesses this small are used preferably in femcare napkins, in incontinence pads or else in wound contact materials.

The basis weight of the absorbent structure is preferably at least 300 g/m², further preferably at least 320 g/m², further preferably at most 500 g/m², further preferably at most 450 g/m², further preferably at most 400 g/m².

The absorbent structure especially preferably has a relative absorption capacity of at least 18 g/g, further preferably of at least 20 g/g, further preferably of at least 22 g/g, further preferably of at most 40 g/g, further preferably of at most 30 g/g, further preferably of at most 26 g/g, further preferably of at most 24 g/g, with the absorption capacity measured according to the method described below.

Especially preferably, the absorbent structure has a relative retention capacity of at least 7 g/g, further preferably of at least 9 g/g, further preferably of at least 11 g/g, further preferably of at most 18 g/g, further preferably of at most 16 g/g, further preferably of at most 14 g/g, further preferably of at most 12 g/g, the retention capacity being measured according to the method described below.

The absorbent structure may be configured arbitrarily in terms of its two-dimensional extent. Rectangular forms are possible, but so are forms adapted to the particular utility.

In one of its aforementioned embodiments, the absorbent structure of the invention may as such already form an absorbent article or be included in an absorbent article.

Another subject of the invention is an absorbent article which comprises an absorbent structure of the invention according to any of the preceding embodiments. The absorbent article here is preferably an incontinence pad, a femcare napkin, an incontinence diaper of the open type with closure systems, an incontinence diaper of the closed type, and/or a wound contact material.

For the embodiment of the absorbent article as a hygiene article, such as a femcare napkin, an incontinence pad or an incontinence diaper, a liquid-pervious ply is disposed on one of the two outer absorbent plies, and a liquid-impervious ply is disposed on the other of the two outer absorbent plies. Provision is made here more particularly for the liquid-pervious ply to be directed at the body of the user in use, whereas the liquid-impervious ply faces away from the body of the user in use and, in the case of absorbent hygiene products, is oriented toward the clothing.

Liquid-pervious and/or, in particular, body-facing plies comprise a nonwoven web or preferably consist of a nonwoven web. It is especially advantageous if the nonwoven web comprises a spunbond material, a laminate made up of spunbond plies (S) and meltblown plies (M), or a staple fiber web material, or combinations thereof. These nonwoven webs more particularly have a basis weight of at least 6 g/m², more particularly of at least 10 g/m², more particularly of at most 30 g/m², more particularly of at most 20 g/m².

Liquid-impervious plies and/or, in particular, plies facing away from the body advantageously comprise thermoplastic foils or films, more particularly a microporous foil or a web/foil laminate having one of the aforesaid foil or film layer, or consist of the aforesaid materials.

In the preparation of hygiene articles, there is preferably, in addition, a liquid distributor ply inserted between the absorbent structure and the liquid-pervious, more particularly body-facing, ply. The liquid distributor ply may preferably be a nonwoven web material made of PP, PE or polyester fibers.

For the embodiment of the absorbent article as a wound contact material with possibility for fixing to the skin of the user, there is preferably a carrier material, which extends beyond the contour of the absorbent structure, disposed and fixed on one of the two outer absorbent plies. In the case of an adhesive wound contact material, the carrier material has a customary, continuous or else discontinuous coating of a skin-compatible adhesive. The carrier materials preferably have properties such as breathability, water vapor permeability or ready detachability of the adhesive. Carrier materials which can be used include preferably liquid-tight and water vapor-permeable foils of polyester, polyurethane, polypropylene, polyethylene or polyamide, or mixtures thereof. Likewise possible is use of porous carrier materials made of nonwoven web material or textile material, such as woven or knitted fabrics, for example.

The measurement methods used are described in detail below:

Determination of the pH of the First, Second and Third Cellulose Fibers

The determination of the pH of the first and second cellulose fibers is based on DIN 53124—August 1998.

Test equipment needed is as follows: glass conical flask with stopper, precision balance with a read-off accuracy of 0.01 g, thermometer, glass pH electrode with an accuracy of pH=0.05.

Reagents needed are as follows: demineralized water with a conductivity of below 0.1 mS/m, standard buffer solutions (pH 7 and pH 4) for calibrating the pH electrode.

The determination of the pH of the respective cellulose fibers takes place in the solution obtained after cold extraction:

To produce the aqueous extract, a sample amount of cellulose fiber material of 2 g+/−0.1 g is extracted with 100 ml of demineralized water at a room temperature of 23° C.±2° C. at 50% relative humidity for one hour in a sealed glass conical flask. For this purpose, the sample material is shaken at the start and then every 15 minutes.

At the sample preparation stage, the following should be observed: the demineralized water used for the extraction must have a conductivity of below 0.1 mS/m. In the case of an initial mass of cellulose fiber material that deviates from 2.0 g, the volume of demineralized water provided, of 100 ml, should be modified with a corresponding deviation in direct proportion. Furthermore, with regard to the initial mass of cellulose fiber material, the dry matter content of the cellulose fibers must be taken into account. With knowledge of the dry matter content of the cellulose fiber material, the dry matter content when the cellulose fiber material is initially weighed out is taken into account by weighing out an initial mass corresponding to 2.0 g dry mass of the cellulose fiber material.

In the extract obtained in the cold extraction, the pH is measured under standard conditions at 23° C.±2° C. and 50% relative humidity. Before the pH is determined, the pH electrode must be calibrated using standard buffer solutions: the pH electrode used is a combined glass pH electrode with the reference system Ag/AgCl and with 3 mol/l KCl as reference electrolyte, with a conical glass membrane having a pH service range of 0-14 and a zero point at pH=7.0. For this purpose it is possible for example to use the BlueLine 14 pH electrode from SI Analytics of 55122 Mainz, Germany. Standard buffer solutions used can be standard buffer solutions prepared according to DIN 53124: 1998-08, Appendix A, or commercial products. Examples of commercial products which can be used are AVS TITRINORM® pH 4 and AVS TITRINORM® pH 7 from VWR International, 64295 Darmstadt, Germany. After the pH electrode has been calibrated and rinsed repeatedly with demineralized water, the pH measurement in the extract is carried out.

The number of tests is n=3. The result is reported as an average of these three measurements, with rounding to one decimal place.

Determination of the Dry Matter Content of the First, Second and Third Cellulose Fibers Determination of the dry matter content (and hence of the dry mass) of the first, second and third cellulose fibers or of the corresponding cellulose fiber plate is carried out separately before the pH measurement.

For sample preparation, in the case of cellulose fibers pressed into plate form, this cellulose fiber plate is cut or torn into pieces. Sample preparation here must be done rapidly, in order to reduce moisture content losses to a minimum. Sample preparation takes place under standard conditions of 23° C.±2° C./50% relative humidity.

Test equipment needed is as follows: a glass weighing vessel impervious to water vapor, with a tightly sealing lid; a drying cabinet (105±2° C.); a precision balance with a read-off accuracy of 0.0001 g; and a desiccator.

For the test procedure, the glass weighing vessel is initially dried and weighed together with the lid (w1). Then exactly 5 g of cellulose fiber material (m1) are weighed out into the vessel. After weighing has taken place, the weighing vessel with the cellulose fiber material and with the lid removed is placed into the drying cabinet at a constant temperature of 105±2° C. until a constant mass has been reached. The drying period here may be not less than 3 h and also not longer than 16 h. The mass of the test specimen is deemed constant when two successive weighings differ from one another by not than 0.1% of the original mass of the test specimen. When mass constancy has been reached, the weighing vessel is removed from the drying cabinet, the lid is replaced, and it is placed in a desiccator to cool for 45 minutes. After cooling, the weighing vessel is taken from the desiccator and the inner and outer atmospheric pressures of the vessel are balanced by rapidly half-opening and reclosing the lid. The weighing vessel, with its dried contents and lid, is weighed to an accuracy of 0.0001 g (m2). The dry matter content is determined from the following equation:

Dry matter content in %=[(m2−w1)/m1]×100

The number of tests is at least n=3.

Determination of the Relative Absorption Capacity and the Relative Retention Capacity of the Absorbent Structure, in a Method Based on the Teabag Test Test equipment and reagents needed are as follows: teabag web material from Degussa Evonik, web welder, analytical balance with read-off accuracy 0.0001 g, precision balance with read-off accuracy 0.01 g, bowl, drip-dry grid with clips, stopwatch, laboratory centrifuge (1111 rpm, diameter 40 cm, corresponding to acceleration of 276 g with g=9.81 m/s$^2$), and 0.9% sodium chloride solution.

Sample preparation and testing take place under standard conditions at 23° C.±2° C./50% relative humidity.

For sample preparation, tea filter bags are produced from the web material by folding the material about a half-axis, welding is along the side edges, and retaining one open side. Punched sample specimens are taken from the absorbent structure, weighed (=M1), and introduced into the prepared teabag. The open side of the tea filter is then welded closed. In the same way, empty teabags are welded as an illustrative sample.

Sample specimens used were punched specimens 145×45 mm in size.

For the test, the teabags filled with sample specimen were placed for first moistening into the NaCl solution and submerged therein for 30 minutes. Thereafter the teabags are taken from the NaCl solution, before then being left to drip dry, hanging freely with the clip transversely at the weld seam, for 10 minutes, and then being weighed (=M2).

The teabags are subsequently spun for 4 minutes in the laboratory centrifuge and subsequently weighed again (=M3).

As illustrative samples, empty teabags are tested under the same conditions (=M4).

The absorption A after drip-drying is calculated as follows:

$$A=(M2-M4-M1)/M1 \text{ [g/g]}$$

The retention R after spinning is calculated as follows:

$$R=(M3-M4-M1)/M1 \text{ [g/g]}$$

The test takes place using 5 individual measurements on samples and 3 individual measurements on illustrative samples, and the result is reported as an average from these measurements, with rounding to one decimal place.

Further features, advantages, and details of the invention will become apparent from the appended claims and from the representational drawing and subsequent description of preferred embodiments of the invention.

For the features disclosed above and the features expressed below in the claims, patent protection is claimed independently of any dependency reference and in any desired combination with one another.

BRIEF DESCRIPTION OF THE DRAWINGS

The invention is to be elucidated in more detail below with reference to the figures.

DETAILED DESCRIPTION

Figure 1:
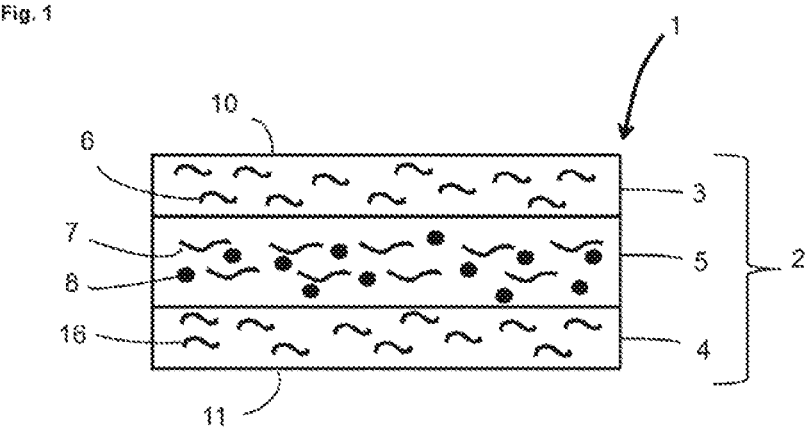
FIG. 1 shows schematically a cross section through an absorbent structure of the invention.

FIG. 1 shows schematically in cross section a preferred absorbent structure 1 having a sequence 2 of interconnected plies. This sequence comprises a first outer absorbent ply 3 of airlaid material, a second outer absorbent ply 4 of airlaid material, and, disposed between these two plies, a liquid storage ply 5 of airlaid material. The first outer ply 3 has first cellulose fibers 6, the second outer ply 4 has second cellulose fibers 16, and the liquid storage ply 5 has third cellulose fibers 7 and superabsorbent components 8. It is essential here that the first and second cellulose fibers 6, 16 differ in their pH from the pH of the third cellulose fibers 7. The pH of the first and second cellulose fibers 6, 16 is lower than the pH of the second cellulose fibers 7. The pH of the first and second cellulose fibers is below pH 5.0. With further preference the pH of the first and/or second cellulose fibers is below 4.7, preferably below 4.5, preferably below 4.2, and further preferably above 3.2, further preferably above 3.5, further preferably above 3.7, further preferably above 3.9. The pH of the cellulose fibers is determined by the method described. As a result of both outer absorbent plies being equipped with acidic first and second cellulose fibers 6, 16, respectively, the absorbent structure 1 can be disposed flexibly in direct use and also within an absorbent article, such as an incontinence pad, for example. Independently of the orientation of the absorbent structure, an outer absorbent ply including acidic cellulose fibers is always directed at the skin of the user and is able to effect the positive growth-inhibiting properties ascribed to the plies with respect to microorganisms. The pH of the first and/or second cellulose fibers differs from the pH of the third cellulose fibers preferably by no less than 0.5 and not more than 3.0. The pH of the first and/or second cellulose fibers preferably differs from the pH of the third cellulose fibers by not more than 2.0.

Cellulosic material employed for the first, second, and third cellulose fibers is preferably fluff pulp. As first and/or second cellulose fibers it is possible with preference to use reaction products of the cellulosic material fluff pulp with polycarboxylic acids, such as citric acid, for example.

Figure 2:
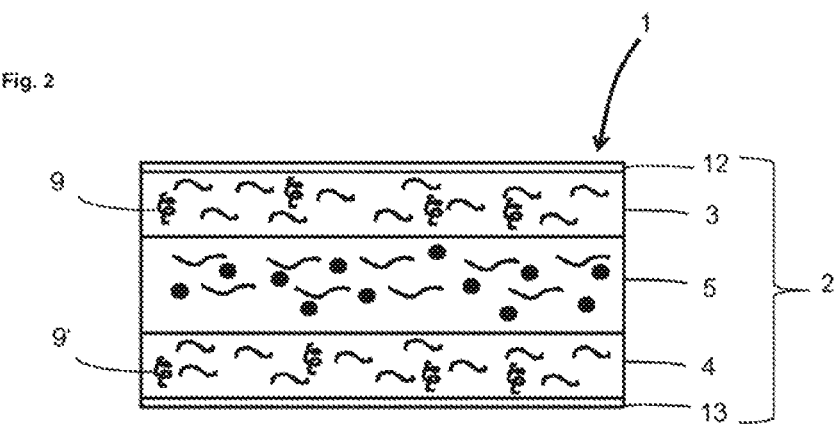
FIG. 2 shows schematically a cross section through a further embodiment of an absorbent structure of the invention.

The airlaid materials of plies 3, 4 and 5 may well be admixed with other staple fibers, but in accordance with the invention in the airlaid materials there is no provision for fiber blending with meltblown fibers or spunbond fibers, but instead only fibers of finite length. Accordingly, in one preferred embodiment of the absorbent structure 1, as shown schematically in FIG. 2, binding fibers 9, 9', more particularly in the form of bicomponent fibers of polyethylene terephthalate and polyethylene, can be included in the airlaid material of the first and second outer absorbent plies 3, 4. The binding fibers make an advantageous contribution to the strength of the outer absorbent plies. However, for differentiating the functionality of the outer absorbent plies relative to the plies disposed in the middle relative to them, such as the liquid storage ply, binding fibers make an advantageous contribution to the transport of the liquid in the direction of the middle to the liquid storage ply 5. On the first and second surfaces 10, 11 of the sequence 2 of the interconnected plies, additionally, there may be a binding agent coating 12, 13 applied, composed of polymeric materials, this coating making an advantageous contribution to the abrasion resistance of the absorbent structure and also to the function of transfer of the liquid into the interior of the absorbent structure. The binding agent coating may be based, for example, on an ethylene-vinyl acetate copolymer.

In one preferred embodiment of the absorbent structure 1, the plies in the sequence 2 have mirror symmetry. More particularly, the sequence 2 consists of first and second outer absorbent plies, 3, 4 and the liquid storage ply 5 disposed between them, as shown schematically in FIG. 1 or 2.

In one particularly preferred embodiment of the absorbent structure 1, the sequence 2 of interconnected plies consists of the first and second outer absorbent plies 3, 4 and, disposed between them, the liquid storage ply 5. The first cellulose fibers 6 in the airlaid material of the first outer absorbent ply 3 and the second cellulose fibers 16 in the airlaid material of the second outer absorbent ply 4 are formed from fluff pulp and have a pH of 3.9-4.2. The third cellulose fibers 7 are similarly formed of fluff pulp, but with a pH of 5.9-6.2. The combined fraction of first and second cellulose fibers 6, 16 of the first and second outer absorbent plies 3, 4 is 30-40 wt % based on the combined weight of the sequence 2 of interconnected structures. The superabsorbent components 8 are incorporated solely in the airlaid material of the liquid storage ply 5, and in a fraction of 40-50 wt % based on the combined weight of the sequence 2. Provision is made for the admixing of binding fibers 9, 9' in the form of bicomponent fibers in the two outer absorbent plies 3, 4, in a total fraction of 4-6 wt % based on the combined weight of the sequence 2. Applied to the two surfaces 10, 11 of the sequence 2 is a binding agent coating 12, 13 in a fraction of at most 5 wt %. The absorbent structure 1 preferably has a basis weight of at least 320 g/m$^2$ and of at most 400 g/m$^2$ with a thickness of 2-4 mm. The relative absorption capacity of the absorbent structure 1 is preferably 22-24 g/g, and the relative retention capacity is preferably 9-12 g/g.

In the case of one particularly preferred embodiment, the two outer absorbent plies are identical at least with regard to the pH of the first and second cellulose fibers; further preferably, the first and second cellulose fibers are identical in their chemical composition or their provenance or origin; with more particular preference, the two outer absorbent plies 3, 4 are identical with regard to all properties.

With this embodiment of the absorbent structure, the absorbent structure can be used within an absorbent article, such as in an incontinence pad, either with the first absorbent ply 3 arranged facing the body or else with the second absorbent ply 4 arranged facing the body, and can therefore be used flexibly, even in an ongoing production process.

The absorbent structure 1 of the invention may as such already be used as an absorbent article. The absorbent structure of the invention may be used preferably for the fabrication of a particular absorbent article, such as, in particular, a femcare napkin, an incontinence pad, an incontinence diaper of open and closed type, or a wound contact material.

Figure 3:
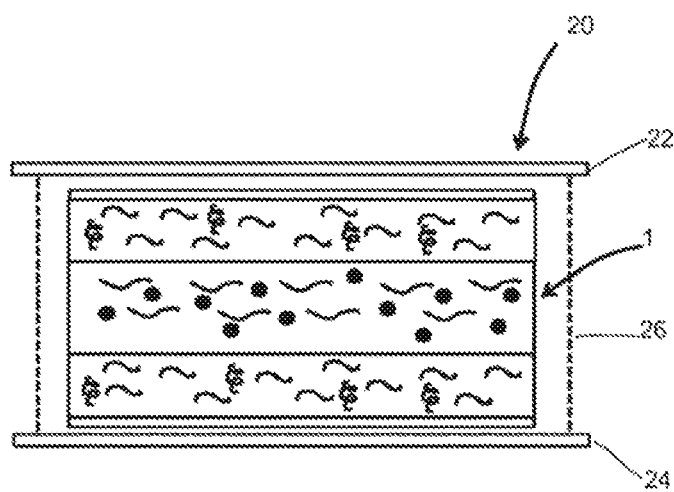
FIG. 3 shows schematically a cross section through an absorbent article with an absorbent structure of the invention.

For an absorbent hygiene article, such as a femcare napkin, an incontinence pad, or an incontinence diaper of open or closed type, further plies may be arranged additionally on the outer absorbent plies 3, 4, as is shown schematically in FIG. 3. Hence on the surface of one outer absorbent ply, as the subsequent body-facing ply, there is a liquid-pervious ply 22 disposed, based in particular on a nonwoven fabric, and, on the surface of the other outer absorbent ply, as the subsequent ply facing away from the body, there is a liquid-impervious ply 24 disposed, based in particular on foils. The liquid-pervious and liquid-impervious plies 22 and 24 are extended preferably beyond the edges of the absorbent structure 1 and are joined to one another by fixing means 26, such as adhesive or weld seam, for example.

Testing for Antimicrobial Activity of the First or Second Cellulose Fibers, Based on the Liquid Method According to AATCC 174-2007

The test method serves for quantitative determination of the antimicrobial activity of the first or second cellulose fibers. For this test, the cellulose fiber material, taken up in Ringer solution, is inoculated with the respective bacterial strain. Determinations of microbe count are carried out after defined times.

The following are needed for the experiment:
sterile scissors, sterile tweezers
sterile bottles, petri dishes, test tubes
incubator (37° C.±2° C.)

Ringer solution: the Ringer solution is prepared by dissolving one Ringer tablet (available from Merck under material number 1.15525.0001) in 500 ml of distilled water. One Ringer tablet contains 0.00525 g of ammonium chloride, 0.005 g of sodium hydrogen carbonate, 0.04 g of calcium chloride dihydrate, 0.00525 g of potassium chloride and 1.125 g of sodium chloride.

Ringer solution with disinhibitors (0.3% lecithin, 0.1% histidine, 1% Tween).

CASO agar=casein peptone/soy flour peptone agar (available from Merck under material number 1.05458.0500)

CASO broth (available from Merck under material number 1.05459.0500)

bacterial strains: *Staphylococcus aureus* ATCC 6538 (DSM 346), *Klebsiella pneumonia* ATCC 4352 (DSM 789)

Preparation:

The bacterial culture for inoculating the samples is obtained from an inoculation culture, taken from the parent culture, and by enrichment of the inoculation culture in a CASO broth for 18-24 hours. For the experiment, the respective bacterial strain is used with colonies of $1$-$5\times10^6$ CFU/ml (CFU=colony-forming units).

Each sample, before the experimental procedure and before inoculation with the microbes, is sterilized by means of ethylene oxide in a validated process (780 mg/1; 240 min, 43-45° C.).

Samples here are understood to be the batches containing cellulose fibers, and also the control batches without cellulose fibers.

A sample batch of the cellulose fibers in each case is prepared with defined fiber material in a defined volume of Ringer solution. In the test procedure, the microbe count employed is additionally verified; in other words, all of the steps in the test procedure are carried out without introduction of cellulose fibers (this is referred to as the microbe count control). In addition, a buffer of pH 3.7 (0.9% NaCl solution adjusted to a pH of 3.7 using HCl solution) is run without using cellulose fibers.

For each sample a triplicate determination at test times time 1=0 h (i.e., immediately, directly after inoculation of the sample batch with bacterial strains), time 2=4 h and time 3=24 h is provided.

Experimental Procedure:

For the microbe count determination, each sample batch is placed in a sterile 250 ml bottle with a screw closure and is inoculated with 1 ml of the bacterial culture ($1$-$5\times10^6$ CFU/ml). Then 100 ml of sterile Ringer solution are added.

For the determination of the instantaneous value, i.e., time 1=0 h, 1 ml of the sample batch is taken straight after the Ringer solution has been added, and is plated out on a sterile petri dish with CASO agar. The sample batches as such are then incubated in the bottles in the incubator at 37° C.±2° C. and processed further accordingly for the further defined times:

After the respective growth times (0 h, 4 h, 24 h), the screw-closure vessels are treated in an ultrasound bath for 1 minute and then shaken mechanically for 1 minute. Subsequently, a dilution series is prepared from the samples, by introducing 1 ml in each case from the preceding solution into a sterile tube already containing 9 ml of Ringer solution with disinhibitor. The dilution series are prepared in such a way as to allow subsequent counting of the colonies that have grown. In the case of batches with a relatively high anticipated bacterial growth, such as the microbe count controls, higher dilutions are prepared, accordingly.

Subsequently, using a sterile pipette, 1 ml is taken from each dilution stage and pipetted into a sterile petri dish, and coated with 15-20 ml of agar medium (CASO agar). For the uniform distribution of the medium, the filled petri dishes are moved in a circular motion over the work surface. After the agar has solidified, the petri dishes are placed with the lid downward into the incubator and are incubated in the incubator at 37±2° C. for 18-24 hours.

The microbe counts are then evaluated by counting the microcolonies that have grown. In the case of relatively vigorous colony growth, the plates with colonies between 30 and 300 are employed for the evaluation, and the count values of two dilution stages are taken into account as far as possible.

The mean estimated colony count is determined as follows:

$$x_m = \frac{\text{Total colony count value}}{\text{Total dilution stages}} \text{ e.g.,}$$

$$x_m = \frac{303 + 290 + 32 + 28}{10^{-4} + 10^{-4} + 10^{-5} + 10^{-5}} = \frac{653}{2.2 \times 10^{-4}} = 2.97 \times 10^6$$

The values determined are then expressed in the unit CFU/ml.

Example: Testing of the Antimicrobial Activity of First or Second Cellulose Fibers in Comparison to Third Cellulose Fibers The cellulose fibers and the reagents are sterilized as described above prior to inoculation.

The following sample batches are selected:
 4 g of first or second cellulose fibers with a pH of 3.9-4.1, Ringer solution ad 100 ml without disinhibitors
 4 g of third cellulose fibers with a pH of 5.9-6.2, Ringer solution ad 100 ml without disinhibitors
 microbe count control: 100 ml of Ringer solution without disinhibitors
 pH control: 100 ml of buffer pH 3.7 (0.9% NaCl solution adjusted to a pH of 3.7 with HCl solution)

The experimental procedure then takes place as described above. Each sample batch is inoculated with 1 ml of the bacterial culture ($1$-$5\times10^6$ CFU/ml). The microbe count determinations are made after the incubation times of time 1=0 h, time 2=4 h and time 3=24 h.

Figure 4:
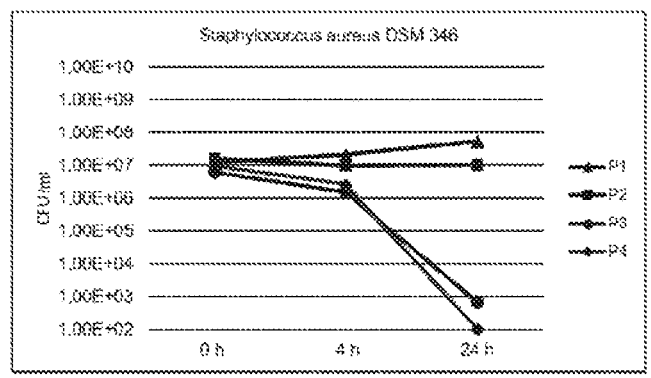
FIG. 4 shows diagram 1 relating to the antimicrobial activity of the first or second cellulose fibers in comparison to the behavior of the third cellulose fibers in the case of *Staphylococcus aureus* DSM 346.
Figure 5:
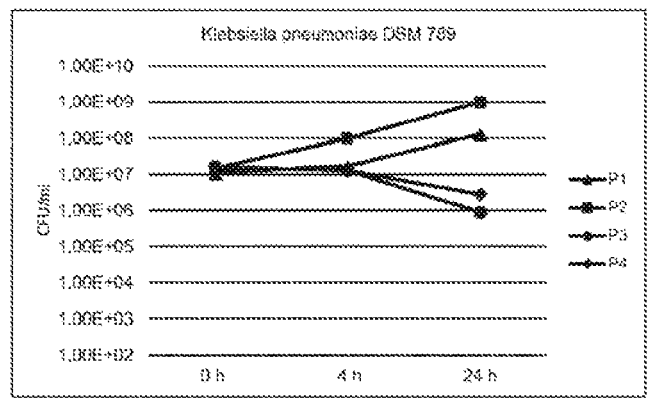
FIG. 5 shows diagram 2 relating to the antimicrobial activity of the first or second cellulose fibers in comparison to the behavior of the third cellulose fibers in the case of *Klebsiella pneumoniae* DSM 789.

The results in table 1, and in the diagram 1 shown in FIG. 4, and in table 2, and in the diagram 2 shown in FIG. 5, show the antimicrobial activity of the first or second cellulose fibers in comparison to the behavior of the third cellulose fibers.

TABLE 1

Antimicrobial activity with experimental microbe *Staphylococcus aureus* DSM 346

|  |  | After 0 h (instantaneous) [CFU/ml] | After 4 h [CFU/ml] | After 24 h [CFU/ml] |
|---|---|---|---|---|
| Microbe count control | P1 | 1.20E+07 | 2.10E+07 | 5.30E+07 |
| Third cellulose fibers | P2 | 1.60E+07 | 9.50E+06 | 1.00E+07 |
| First or second cellulose fibers | P3 | 6.10E+06 | 1.50E+06 | 6.70E+02 |
| Buffer pH 3.7 | P4 | 9.40E+06 | 2.60E+06 | 1.00E+02 |

TABLE 2

Antimicrobial activity with experimental
microbe *Klebsiella pneumoniae* DSM 789

|  |  | After 0 h (instantaneous) [CFU/ml] | After 4 h [CFU/ml] | After 24 h [CFU/ml] |
|---|---|---|---|---|
| Microbe count control | P1 | 1.10E+07 | 1.70E+07 | 1.30E+08 |
| Third cellulose fibers | P2 | 1.50E+07 | 1.00E+08 | 9.90E+08 |
| First or second cellulose fibers | P3 | 1.60E+07 | 1.30E+07 | 8.90E+05 |
| Buffer pH 3.7 | P4 | 1.50E+07 | 1.30E+07 | 2.80E+06 |

The invention claimed is:

1. An absorbent structure having a sequence of interconnected plies comprising:
   a first outer absorbent ply of airlaid material,
   a second outer absorbent ply of airlaid material, and
   disposed between the first and second outer absorbent plies a liquid storage ply of airlaid material, wherein:
      the airlaid material of the first outer absorbent ply includes first cellulose fibers,
      the airlaid material of the second outer absorbent ply includes second cellulose fibers, and
      the airlaid material of the liquid storage ply includes third cellulose fibers and superabsorbent components,
      wherein the first and second cellulose fibers have a lower pH than the third cellulose fibers and a pH of the first and second cellulose fibers is below 5.0.

2. The absorbent structure according to claim 1, wherein one or more of the first or second cellulose fibers have a pH above 3.2.

3. The absorbent structure according to claim 1, wherein the third cellulose fibers have a pH below pH 7.0.

4. The absorbent structure according to claim 1, wherein the airlaid material of the liquid storage ply includes no first and no second cellulose fibers.

5. The absorbent structure according to claim 1, wherein the first and second cellulose fibers of the first and second outer absorbent plies are present in a total proportion of 20-50 wt % based on the combined weight of the sequence of interconnected plies.

6. The absorbent structure according to claim 1, wherein one or more of the first, second, or third cellulose fibers consist of or contain cellulosic fibrous material from the group of cotton fibers and/or fluff pulp.

7. The absorbent structure according to claim 1, wherein one or more of the first or second cellulose fibers are reaction products of cellulosic fibrous material with polycarboxylic acids or salts thereof and/or polyacrylic acids or salts thereof.

8. The absorbent structure according to claim 1, wherein the airlaid material of one or more of the first or second outer absorbent plies includes no superabsorbent components.

9. The absorbent structure according to claim 1, wherein the superabsorbent components of the liquid storage layer are present in a proportion of not less than 25 wt % based on the combined weight of the sequence of interconnected plies.

10. The absorbent structure according to claim 1, wherein the airlaid material of one or more of the first or second outer absorbent plies includes binding agents.

11. The absorbent structure according to claim 1, wherein the airlaid material of the liquid storage ply includes no binding fibers.

12. The absorbent structure according to claim 1, wherein the sequence of interconnected plies includes first and second outer surfaces and one or more of the first or second outer surfaces include a binding agent coating.

13. The absorbent structure according to claim 1, wherein the first and second outer absorbent plies are identical with regard to one property at least, this property being taken from the group containing basis weight, pH of first and second cellulose fibers, chemical composition or natural provenance or origin of first and second cellulose fibers, weight fraction of first and second cellulose fibers, weight fraction of binding fibers, or fiber blend used for the airlaid material.

14. The absorbent structure according to claim 13, wherein the first and second outer absorbent plies are at least identical with regard to the pH of the first cellulose fibers and the pH of the second cellulose fibers.

15. The absorbent structure according to claim 13, wherein the first and second outer absorbent plies are identical with regard to the pH of the first and second cellulose fibers and with regard to the weight fraction of first and second cellulose fibers.

16. The absorbent structure according to claim 13, wherein the first and second outer absorbent plies are identical with regard to the pH of the first and second cellulose fibers and with regard to the chemical composition or the natural provenance or the origin of the first and second cellulose fibers.

17. The absorbent structure according to claim 13, wherein the first and second outer absorbent plies are identical with regard to the pH of the first and second cellulose fibers and with regard to the chemical composition or the natural provenance or the origin of the first and second cellulose fibers and with regard to the weight fraction of the first and second cellulose fibers.

18. The absorbent structure according to claim 13, wherein the first and second outer absorbent plies are identical with regard to all properties.

19. The absorbent structure according to claim 1, wherein the sequence of interconnected plies has mirror symmetry.

20. The absorbent structure according to claim 1, wherein the absorbent structure forms an absorbent article or is included in an absorbent article.

21. An absorbent article comprising an absorbent structure according to claim 1.

22. The absorbent article according to claim 21, wherein the absorbent article is an incontinence pad, a femcare napkin, an incontinence diaper of the open type with closure systems, an incontinence diaper of the closed type, and/or a wound contact material.

23. The absorbent structure according to claim 3, wherein the third cellulose fibers have a pH above pH 5.0.

24. The absorbent structure according to claim 1, wherein the pH of one or more of the first or second cellulose fibers differs from the pH of the third cellulose fibers by not less than 0.5.

25. The absorbent structure according to claim 9, wherein the superabsorbent components of the liquid storage layer are present in a proportion of not more than 70 wt % based on the combined weight of the sequence of interconnected plies.

26. The absorbent structure according to claim 24, wherein the pH of one or more of the first or second cellulose fibers differs from the pH of the third cellulose fibers by not more than 3.0.

27. The absorbent structure according to claim 1, wherein the airlaid material of one or more of the first or second outer absorbent plies includes no third cellulose fibers.

28. The absorbent structure according to claim 1, wherein the airlaid material of one or more of the first outer or second outer absorbent plies includes binding fibers in a total proportion of 2-10 wt % based on the combined weight of the sequence of interconnected plies.

\* \* \* \* \*